United States Patent [19]

Levy

[11] Patent Number: 5,296,583
[45] Date of Patent: Mar. 22, 1994

[54] CALCIFICATION-RESISTANT SYNTHETIC BIOMATERIALS

[75] Inventor: Robert J. Levy, Ann Arbor, Mich.

[73] Assignee: University of Michigan, Ann Arbor, Mich.

[21] Appl. No.: 910,941

[22] Filed: Jul. 9, 1992

[51] Int. Cl.$^5$ .............................................. C08G 18/38
[52] U.S. Cl. ........................................ 528/72; 528/59; 528/60
[58] Field of Search ............................ 528/72, 59, 60

[56] References Cited

U.S. PATENT DOCUMENTS 4,259,472  3/1981  Chattha et al. ........................ 528/72

Primary Examiner—Maurice J. Welsh
Attorney, Agent, or Firm—Rohm & Monsanto

[57] ABSTRACT

Synthetic biomaterials are provided with irreversibly bound amino diphosphonate, polyphosphonate, or other anticalcification agent to prevent in vivo calcification. Such biomaterials include biocompatible elastomers such as polyurethane and/or polydimethylsiloxane, and the like which are intended for invasive, or in-dwelling use in a human or animal body. Illustratively, reaction conditions utilizing bi- or polyfunctional epoxides result in epoxide bridge incorporation of the anticalcification agent to the biomaterial elastomer.

8 Claims, 4 Drawing Sheets

CALCIFICATION-RESISTANT SYNTHETIC BIOMATERIALS

GOVERNMENT RIGHTS CLAUSE

This invention was made with government support under Contract 5 R01 HL36574 awarded by the National Institutes of Health. The government has certain rights in the invention.

BACKGROUND OF THE INVENTION

This invention relates generally to materials which are resistant to in vivo calcification, and more particularly, to calcification-resistant biomaterials, suitable for implantation in a living being, comprising a synthetic biocompatible polymer to which an anticalcification agent(s) is bound by stable, irreversible covalent bonds.

More than 100,000 cardiac valve prostheses are placed in patients each year. Frequently, valve replacement surgery is the only means of treating cardiac valve disease. Currently used replacement valves include mechanical valves which may be composed entirely of a synthetic polymeric material such as polyurethane; bioprosthetic valves derived from bovine pericardium or porcine aortic valves; and aortic homografts.

Use of mechanical valves is frequently complicated by thrombosis and tissue overgrowth leading to valvular failure. Calcification is the most frequent cause of the clinical failure of bioprosthetic heart valves fabricated from porcine aortic valves or bovine pericardium. Human aortic homograft implants have also been observed to undergo pathologic calcification involving both the valvular tissue as well as the adjacent aortic wall albeit at a slower rate than the bioprosthetic heart valves. Pathologic calcification leading to valvular failure, in such forms as stenosis and/or regurgitation, necessitates re-implantation. Therefore, the use of bioprosthetic heart valves and homografts has been limited because such tissue is subject to calcification.

Pathologic calcification also further complicates the use of synthetic vascular grafts and other artificial heart devices, such as ventricular assist systems, because its affects the flexibility of the synthetic polymers used to produce the devices.

The mechanism for pathological calcification of cardiovascular tissue is not understood. Generally, the term "pathologic calcification" refers to the deposition of calcium phosphate mineral salts in association with a disease process. Calcification may be due to host factors, implant factors, and extraneous factors, such as mechanical stress. There is some evidence to suggest that deposits of calcium are related to devitalized cells, and in particular, cell membranes, where the calcium pump ($Ca^{+2}$-$Mg^{+2}$-ATPase) responsible for maintaining low intracellular calcium levels is no longer functioning or is malfunctioning. Calcification has been observed to begin with an accumulation of calcium and phosphorous, present as hydroxyapatite, which develops into nodules which can eventually lead to valvular failure.

Research on the inhibition of calcification of bioprosthetic tissue has focussed on tissue pretreatment with either detergents or diphosphonates. Both of the aforementioned compounds tend to wash out of the bioprosthetic tissue with time due to blood-material interactions. Thus, these treatments merely delay the onset of the inevitable calcification process. To date, long-term prevention of calcification has been an unattainable result. Accordingly, there is a need for a means of providing long-term calcification resistance for bioprosthetic or synthetic heart valves and other implantable, or in-dwelling, devices which are subject to in vivo pathologic calcification.

Systemic use of anticalcification agents, such as diphosphonates, results in significant side effects on bone, and overall, growth. Site specific therapy offers treatment with low regional drug levels and minimal side effects.

It is, therefore, an object of this invention to provide biomaterials for implantation in a mammal which have increased resistance to in vivo pathologic calcification.

It is another object of this invention to provide biomaterials for implantation in a mammal which have a long-term, or prolonged, resistance to in vivo pathologic calcification.

It is also an object of this invention to provide biomaterials for implantation in a mammal which have localized calcification inhibition and, hence, avoid the toxic side effects associated with systemic administration of anticalcification agents.

It is a further object of this invention to provide new synthetic biomaterial elastomers with increased utility due to retention of flexibility over an extended period of time.

It is additionally an object of this invention to provide a method of fabricating and/or treating biomaterials for implantation in a mammal to render the biomaterials resistant to in vivo pathologic calcification.

It is yet a further object of this invention to provide a novel method of covalently bonding anticalcification agents, specifically polyphosphonates or other anticalcification agents bearing functionalities capable of epoxide derivatization, to biomaterials.

It is also another object of this invention to provide a novel method of irreversibly binding polyphosphonates to synthetic biomaterials for permanent calcification inhibition.

SUMMARY OF THE INVENTION

The foregoing and other objects are achieved by this invention which provides, in one aspect thereof, a biomaterial for implantation in the interior of the body of a living being. The biomaterial has irreversibly bound thereto an effective amount of an anticalcification agent for rendering said biomaterial resistant to in vivo pathologic calcification.

The anticalcification agent(s) is bound to the synthetic biomaterial by a novel epoxide-based derivatization scheme, herein referred to as "epoxy-bridge incorporation," which results in stable, irreversible covalent bonding of the anticalcification agent to the synthetic biomaterial through epoxide linkages. FIG. 1 shows an illustrative reaction scheme and the resulting product, which, in this embodiment, is a phosphonated polyurethane.

The term "biomaterial" as used herein denotes any synthetic biocompatible polymeric material which is known, or becomes known, as being suitable for in-dwelling uses in the body of a living being, i.e., which is biologically inert and physiologically acceptable, nontoxic, and insoluble in the environment of use.

Illustrative biomaterials suitable for use in the practice of the invention include naturally-derived polymers, such as cellulose or collagen-based materials, or synthetic polymers, whether hydrophilic or hydrophobic, including without limitation, polyurethane, polydimethylsiloxane, ethylene vinyl acetate, polymethyl methacrylate, polyamide, polycarbonate, polyester, polyethylene, polypropylene, polystyrene, polyvinyl chloride, polytetrafluoroethylene, polysulfone, or cellulose acetate. It is to be understood that the term polymer is to be construed to include copolymers, such as the copolymer of polyurethane and silicone.

In preferred embodiments, the anticalcification agent is an amino diphosphonate or other polyphosphonate.

Exemplary diphosphonates include 3-amino-1-hydroxypropane-1,1-diphosphonic acid (AHDP) and ethanehydroxydiphosphonate (EHDP). In certain embodiments, other polyphosphonates, such as aminomethyltriphosphonic acid and butylpentaphosphonic acid are preferred. As used herein the term "polyphosphonate" includes compounds having two or more phosphonates per molecule. Such polyphosphonates are commercially available or can be synthesized by those of skill in the art. Additional illustrative examples include, without limitation, hexamethylenediaminetetra(methylenephosphonic acid) and diethylenetriaminepenta(methylenephosphonic acid). Of course, other amino-containing anticalcification agents, such as amino derivatives of phosphocitrate, would be suitable for incorporation into the practice of the invention.

Since the anticalcification agents are irreversibly bound to the biomaterial substrate by epoxide linkages, any anticalcification agent which has amine, amide, alcohol, or carboxylic acid functionalities, for example, can be linked to a biocompatible elastomer via epoxy-bridge incorporation as described herein. Examples of other anticalcification agents include, without limitation, sulfaminotricarballyate, alpha amino oleic acid, pyrophosphate, statherin, polylysine, and polyarginine.

In a method aspect of the invention, synthetic calcification-resistant biocompatible polymeric materials are made by incorporation of polyphosphonate during primary polymerization of a biocompatible polymer or copolymer. In a specific illustrative embodiment, a calcification-resistant synthetic polyurethane is fabricated by the steps of:

forming a monoadduct of a polyphosphonate anticalcification agent and a reactive polyfunctional epoxide;

adding the monoadduct to a prepolymer base, illustratively tetramethylene glycol;

adding diisocyanate as the second component of the polyurethane; and polymerizing the resultant mixture.

Illustrative polyfunctional epoxides which are suitable for use in the practice of the invention include diglycidyl butanediol ether, ethanediol diglycidyl ether, butanediol diglycidyl ether, and polyglycerol polyglycidyl ethers.

In still further method embodiments of the invention, synthetic calcification-resistant biocompatible polymeric materials are made by incorporation of polyphosphonate into prepolymerized biocompatible polymeric materials. In one specific illustrative embodiment, a solution of a polyphosphonate anticalcification agent and a reactive polyfunctional epoxide is formed in a solvent; a pre-polymerized biocompatible polymer which is soluble in the same solvent is added to the polyphosphonate/polyfunctional epoxide solution to form a mixture; and the mixture is polymerized. Of course, the pre-polymerized polymer could be dissolved in the same, or a compatible, solvent prior to contact with the polyphosphonate/polyfunctional epoxide solution.

BRIEF DESCRIPTION OF THE DRAWING

Comprehension of the invention is facilitated by reading the following detailed description, in conjunction with the annexed drawing, in which.

DETAILED DESCRIPTION

Figure 1:
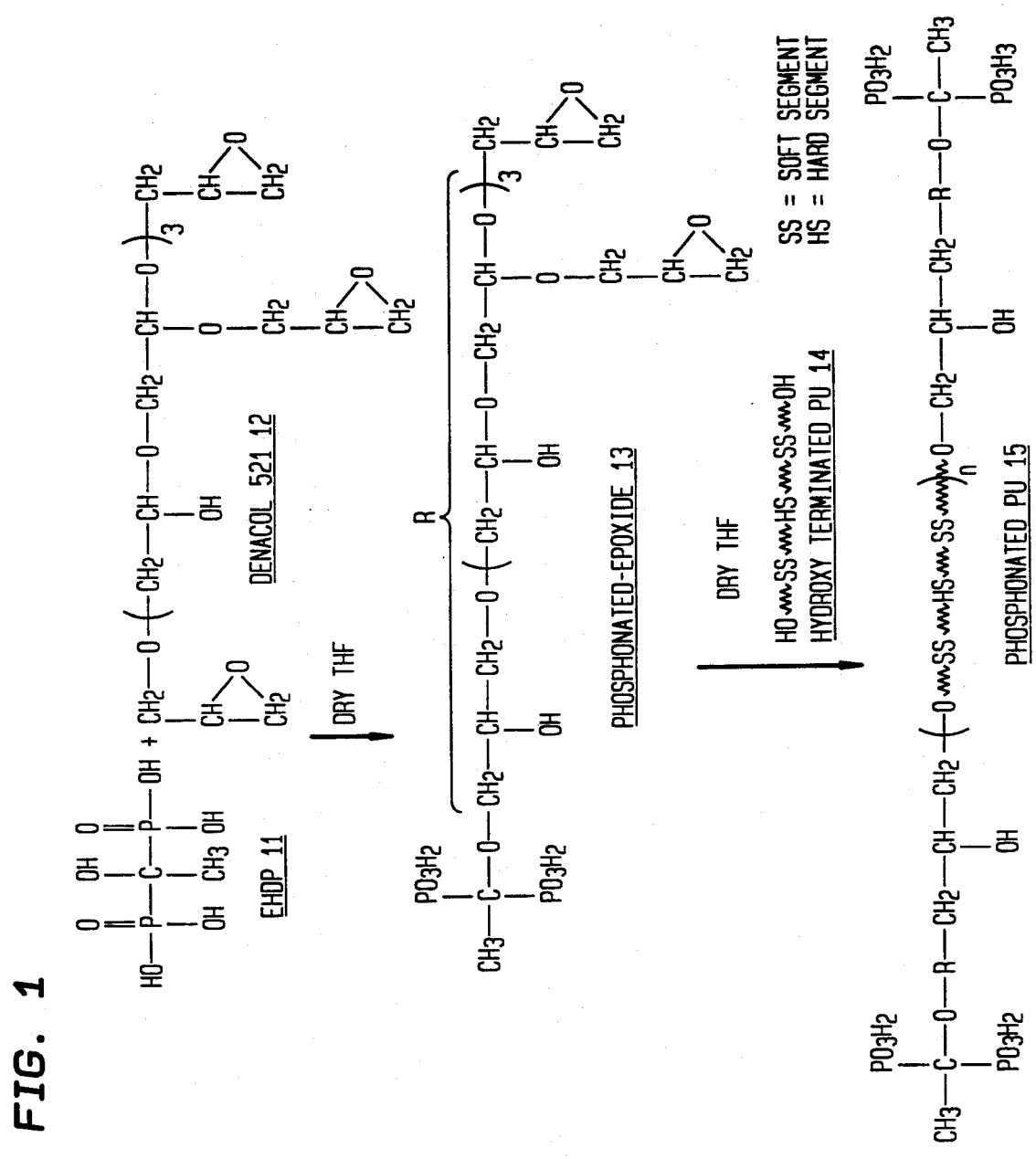
FIG. 1 is an illustrative reaction scheme for linking an anticalcification agent to synthetic biomaterials in accordance with the principles of the invention herein.

Given below are several specific illustrative techniques for producing calcification-resistant synthetic biomaterials in accordance with the principles of the invention. Although the examples given are primarily directed to the preparation of calcification-resistant heart valve components, the techniques described herein are applicable to the creation of any other device, prosthesis, or implant comprising biomaterials of the type used for in-dwelling or surgically implanted devices. Such additional examples include, other cardiovascular devices, such as artificial hearts and ventricular assist systems, urinary catheters, and orthopedic devices which are also subject to pathologic calcification. In its broadest sense, the calcification-resistant materials can be configured to encompass, inter alia, knit or woven fabrics, single or plural filaments, extruded, cast or molded items, coatings on polymeric substrates or biological tissues, etc.

In accordance with the principles of the invention, polyphosphonate anticalcification agents have been successfully bound to synthetic biocompatible polymeric materials, such as medical grade polyurethane, by epoxy derivatization techniques. These techniques, using reactive bifunctional or polyfunctional epoxides, result in stable, irreversible covalent bonding of the diphosphonates to the biomaterial substrate (see Table I and FIGS. 2 and 3). The following procedures have resulted in the incorporation of 100 to 500 nM/ng polyphosphonate anticalcification agent into the polymeric material (see Table II).

It should be noted that the concentration range for the bound diphosphonate salt is given for purposes of illustration only, and can be varied by those of skill in the art because it is greatly in excess of the therapeutically effective amount. The ability to irreversibly bind a high concentration of anticalcification agent to the biomaterial (see FIG. 3), thereby directly placing a high concentration of pharmaceutic at the potential site of calcification over an extended period of time, is a significant advantage of this invention over the prior art.

Illustrative reactive bifunctional or polyfunctional epoxides suitable for use in the practice of the invention include, without limitation, diglycidylbutanediol ester (GAB), ethanedioldiglycidyl ester, erythritol anhydride (EDE), butanediol diglycidyl ether (BDE), or the polyfunctional epoxides sold under the trademark Denacol by Nagasi Chemicals, Osaka, Japan. The Denacol epoxides are polyfunctional polyglycerol polyglycidyl ethers. For example, Denacol 512 has 4 epoxides per molecule and Denacol 521 (see FIG. 1, compound 12) has 5 epoxides per molecule.

Commercially available medical grade elastomers suitable for the practice of the invention include, in preferred embodiments, polyurethanes, or block copolymers which contain high molecular weight macroglycols linked together by a urethane group. Generally, polyurethane elastomers are produced by the rearrangement polymerization of diisocyanate and macroglycols. The main constituents are diisocyanate, a long chain, hydroxyl-terminated macroglycol as either a polyester or a polyether, and a chain extender, such as a short chain glycol or diamine. Illustrative examples include, without limitation, Thiomer or Tecoflex 80A or 60A (trademarks of Thermedics Corp., Woburn, Mass.); polyurethane PU-2000 sold by CarboMedics Corporation, Austin Tex.; Biomer (an aromatic co(-polyetherurea) available from Ethicon, Somerville, N.J.); Cardiothane (a silicone-urethane copolymer available from Kontron, Inc., Evertt, Mass.); or Pellathane, a polyurethane sold by Dow Chemical, Midland, Mich.

In specific advantageous embodiments of the invention, the anticalcification agent is a diphosphonate, such as ethanehydroxydiphosphonate (EHDP) or aminopropanehydroxydiphosphonate (APDP), or a polyphosphonate, such as aminomethyltriphosphonic acid and butylpentaphosphonic acid. Other phosphonate anticalcification agents, however, are suitable for use in the practice of the invention. Moreover, any other anticalcification agent which is known, or becomes known, and has amine, amide, alcohol, or carboxylic acid functionalities, for example, can be linked to a biocompatible elastomer via the epoxide derivitization techniques described herein.

Other such anticalcification agents include sulfamino-tricarballylate (*Analyt. Biochem.*, Vol. 132, p. 115, 1983); alpha-amino-oleic acid, *Trans. Soc. Biomat.*, Vol. XIV. p. 60, 1991); pyrophosphoric acid, *Science*, Vol. 165, p. 1264, 1969); and the anticalcification protein, statherin and protamine sulfate (*J. Biomed. Mater. Res.*, Vol. 25, p. 85, 1991); polylysine; and polyarginine.

In certain preferred embodiments, it is necessary to use the acid form since salts of polyphosphonates are not soluble in the organic solvents used in the reactions. Acid EHDP may be purified from a commercially available acid form or from the disodium salt. Acid EHDP (crude) is commercially available from Monsanto Chemical, St. Louis, Mo. under the trade mark Dequest 2010. Disodium acid EHDP is commerically available from Norwich Pharmaceuticals, Norwich, N.Y.

Illustratively, the crude acid form or the disodium salt of EHDP is purified on a cation exchange resin, Dowex-50W ($50\times4$-400; Dow Chemical Company, Midland, Mich.). The Dowex-50 resin is conditioned with alternating washes of 1M sodium hydroxide and 1M hydrochloric acid through seven cycles in a Buchner funnel. The final washing is done with hydrochloric acid. The resin is then washed with double distilled water until the pH of the effluent corresponds to the pH of the double distilled water. The resin is stored in water until use.

An appropriate ratio of EHDP to ion exchange resin is 1 g of EHDP in 100 ml water to 32 g of resin. The resin mixture is stirred for four hours at room temperature. The Dowex-50 resin has a high capacity for sodium, and other cationic contaminants, and completely exchanges these contaminants with hydrogen to yield a pure solution of acid EHDP. The supernatant is then decanted from the resin and freeze dried under high vacuum. The purified acid EHDP may be recrystallized by any known technique, such as solvent evaporation with seed crystal addition.

A. Incorporation of Polyphosphonate During Primary Polymerization

In general, a polyphosphonate or other epoxy-reactive anticalcification agent will be combined with a polyepoxide in a solution under reactive conditions, which will result in both adduct formation of the anticalcification agent with the epoxide, and retention of residual reactive epoxy groups for subsequent reactions with a polyol. The reactive anticalcification-epoxy-bridge compound will then be combined with a polyol or polyether prior to polyurethane polymerization via the usual diisocyanate addition. The unique feature of this general reaction scheme is the use of the polyepoxy compound as an epoxy-bridge forming agent, to incorporate anticalcification compounds within the framework of conventional polyurethane chemistry, or other biocompatible polymer chemistry in general.

Typically, a polyphosphonate anticalcification agent and a reactive polyepoxide are combined in a 1:1 molar ratio in a suitable solvent, such as THF, for a time sufficient to form a monoadduct, illustratively 30 minutes. The monoadduct is combined with a prepolymer base in molar ratios ranging from 1:1 to 5:1 reactive adduct-epoxy groups per each potential hydroxyterminus to form a resin having both the epoxide an the anticalcification agent. The second polymer component is then added to the resin and polymerization is initiated.

In a specific illustrative embodiment, butanediol diglycidyl ether (25 $\mu$l) was added to a 0.1M solution of acid EHDP in 3 ml of dried tetrahydrofuran (THF) and stirred for 30 minutes. The resulting solution was combined with 3.45 g of polytetramethylene glycol (1000 mw) and stirred for an additional 30 minutes at room temperature. Polytetramethylene glycol is the prepolymer base for Tecoflex 80A. The second component of the copolymer, diisocyanate (0.93 g), was added to the solution and stirred until homogeneity was obtained. The polymerization reaction was catalyzed by the addition of 200 $\mu$l acetone-FeCl$_3$ (5 mg/ml). The mixture was then poured into a petri dish to polymerize in a vacuum oven at 100° C. (about 48 hours).

Figure 2:
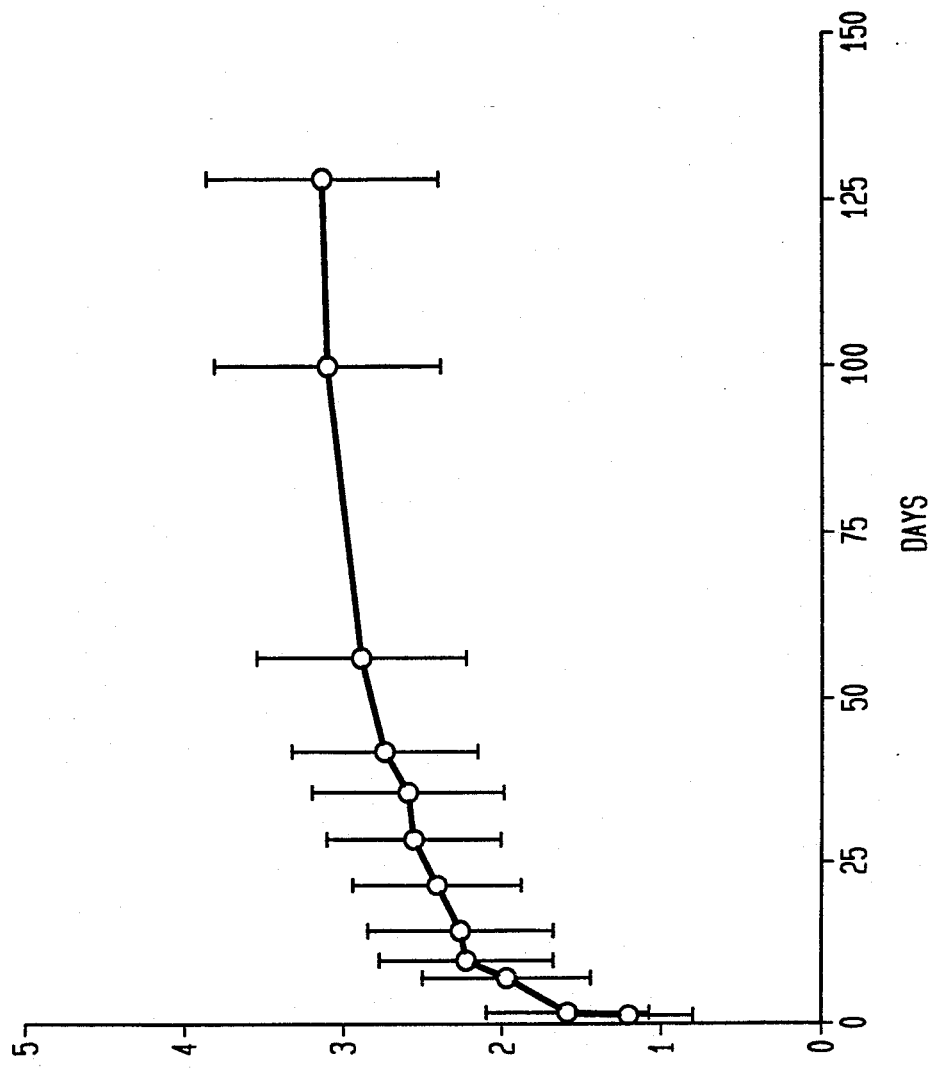
FIG. 2 is a graphical illustration showing dissociation of an anticalcification agent, EHDP, from a calcification-resistant polyurethane matrix fabricated in accordance with a method aspect of the invention.

Release studies were conducted by incorporating radioactive EHDP ($^{14}$C EHDP) into Tecoflex 80A in accordance with the procedure described above. Referring to FIG. 2, the dissociation of epoxy-bridge linked EHDP from the resulting calcification-resistant polyurethane into a physiological buffer (pH 7.4) at 37° C. over a 128 day period is negligible. The data is expressed as the percentage released of the total bound. Thus, approximately 97% of the originally bound EHDP remains after at the 128th day.

The resulting calcification-resistant polyurethane can be dissolved in THF, dimethylacetamide (DMA), or dimethylformamide (DMF), and cast as films or used as coatings. In the alternative, the calcification-resistant polyurethane could be cast into molds.

B. Incorporation of Polyphosphonate Into Prepolymerized Materials

Polyphosphonates can also be irreversibly bound to prepolymerized materials via epoxy-bridge incorporation, illustratively, with hydroxy-terminated polyurethanes or amino-terminated polyurethane ureas, such as Mitrathane MPU5 (a trademark of Mitral Medical, Wheatridge, Colo.) or Biomer (a trademark of Ethicon, Somerville, N.J.).

In general, a polyphosphonate and a polyepoxide are combined in a 1:1 molar ratio in a suitable solvent, such as THF, for a time sufficient to form a monoadduct, illustratively 30 minutes. A prepolymerized polymer, which in some embodiments may be dissolved in a compatible solvent, is combined with the polyphosphonate/polyepoxide monoadduct in a ratio of one mole polymer to one mole epoxy group. The resulting mixture is dried and reacted in a vacuum oven for a period of time, illustratively 24 to 48 hours, at a temperature of about 50° to 75° C.

Referring to FIG. 1, an illustrative reaction scheme shows epoxy-bridge incorporation of a polyphosphonate into a polyurethane in accordance with a method aspect of the invention. A 0.1M solution of acidic EHDP (compound 11) in 2.0 ml THF was made. A reactive epoxide, Denacol-521 (a polyfunctional epoxide with five reactive groups per molecule sold by Nagasi Chemical, Osaka, Japan and shown as compound 12) was added to the EHDP solution in a concentration of 0.1M (148 mg) or 0.02M (29.6 mg). The mixture was stirred for 30 minutes at room temperature to form the monoadduct, or phosphonated-epoxide compound 13. The biocompatible polymeric material, in this case an hydroxy-terminated polyurethane compound 14 (72,000 Mn, 9.0512 g PU-2000 by CabroMedics, Inc., Austin, Tex.) was then added to the EHDP-Denacol mixture and stirred until homogeneous. In other embodiments, amino-terminated polymers, such as Mitrathane MPU5 (11.68 g) or Biomer (10.19 g) are used. Additional solvent (5-10 ml THF) was added to dilute the solution. The solution was then poured into a petri dish and placed in a 60° C. oven. Polymerization was permitted to take place under vacuum over about a 48 hour period. However, the vacuum was not applied until the air bubbles in the solution had disappeared. The result is phosphonated polyurethane compound 15.

Table I below shows the amount of EHDP incorporated (nM/mg) in the polyurethane biomaterial via epoxy-bridge incorporation and the percent released in vitro after 35 days in an isotonic HEPES buffer at pH 7.4 at 37° C. under perfect sink conditions. It should be noted that all EHDP which was not irreversibly covalently bound to the matrix material was released within 48 hours.

TABLE I

| Polyurethane | Epoxy | EHDP Incorporated (nM/mg) | % Released After 35 days |
|---|---|---|---|
| Tecoflex | GAB | 71 | 3.9% |
| Tecoflex | BDE | 72 | 2.0% |
| Biomer | Denacol 521 | 81 | 2.2% |
| Mitrathane MPU5 | Denacol 521 | 68 | 35.5% |

*unbound drug was released within 48 hours

In still further illustrative embodiments of the invention, the diphosphonate EHDP and the polyphosphonates, aminomethyltriphosphonic acid and butylpentaphosphonic acid, were incorporated into pre-polymerized elastomers, specifically polyurethanes and silicone-polyurethane copolymers, in accordance with the procedure set forth above using Denacol 512 as the polyepoxide. Table II shows the amount of incorporated polyphosphonate in nM/mg.

TABLE II

| BASE POLYMER | TYPE OF POLY-PHOSPHONATE | AMOUNT OF POLY-PHOSPHONATE (nM/mg) |
|---|---|---|
| PU-Si | ATMP | 100 |
| PU-Si | ATMP | 500 |
| PU-2000 | EHDP | 100 |
| PU-2000 | EHDP | 200 |
| PU-2000 | EHDP | 300 |
| PU-2000 | EHDP | 400 |
| PU-2000 | EHDP | 500 |
| PU-Si | EHDP | 100 |
| PU-Si | EHDP | 400 |
| PU-Si | EHDP | 500 |
| PU-2000 | DTMP | 100 |

Notes:
1) PU-2000: solvent cast polyurethane (Carbomedics, Inc., Austin, Tx)
2) PU-Si: polyurethane-silicone rubber copolymer (Dow Corning, Midland, MI)
3) EHDP: ethanehydroxydiphosphonate
4) ATMP: aminomethyltriphosphonic acid (Monsanto Chemical, St. Louis, MO)
5) DTMP: butylpentaphosphonic acid (Monsanto Chemical)

Figure 3:
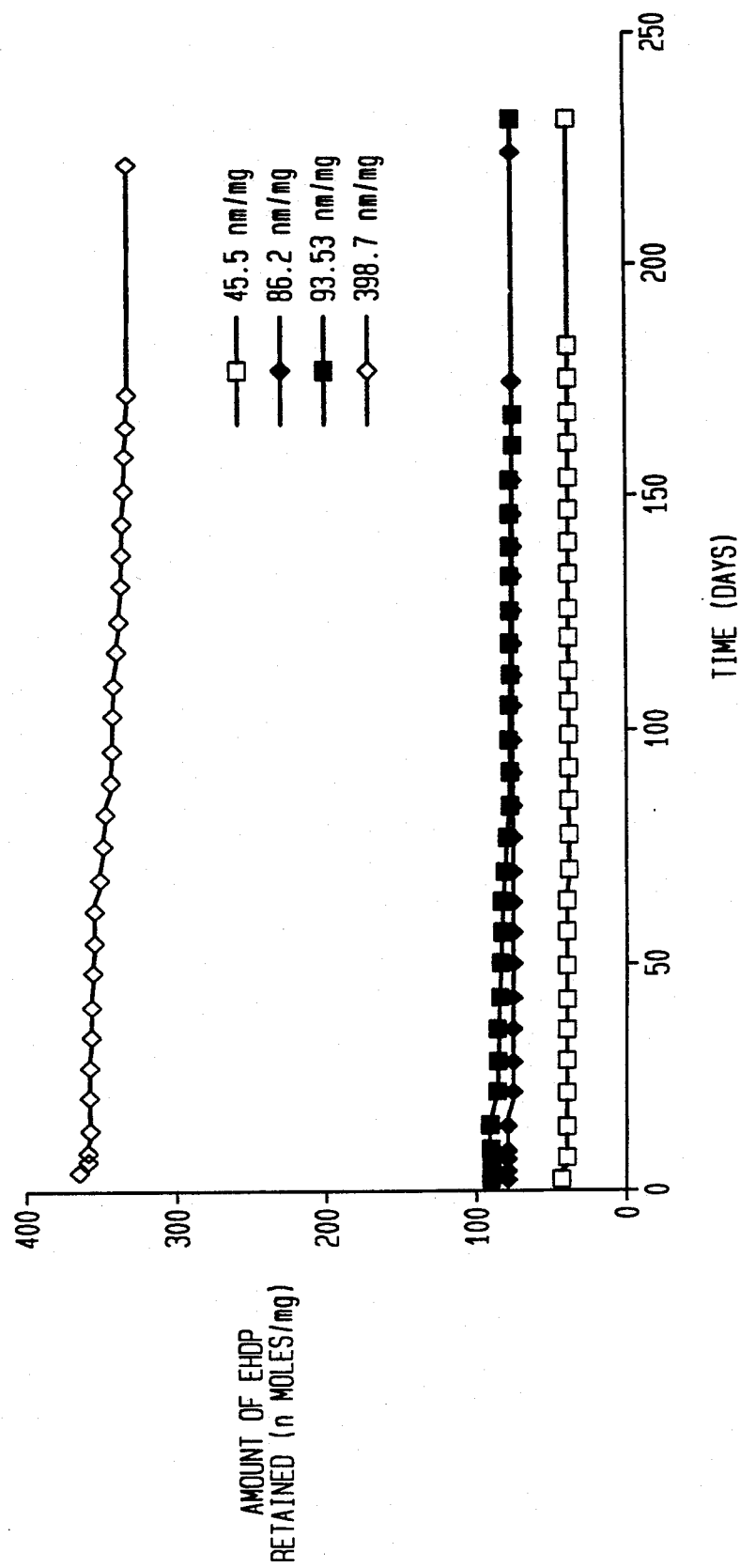
FIG. 3 is a graphical illustration showing the release profile of EHDP from hydroxy-terminated polyurethane matrices fabricated in accordance with a second method aspect of the invention as a function of drug loading.

In addition to the foregoing, an in vitro radioactive diphosphonate ($^{14}C$ EHDP) release study was conducted with several of the polyurethane-EHDP derivatives, formed by the epoxy-bridge incorporation technique, to evaluate release of EHDP from the polyurethane-EHDP matrix over time, and as a function of drug loading. FIG. 3 illustrates the release profile of EHDP from hydroxy-terminated polyurethane matrices as a function of drug loading (45.4 nM/mg to 398.7 nM/mg). As can be seen, there is virtually no significant dissociation of the covalently linked diphosphonate incorporated via this reactive scheme.

The higher phosphonate content polyphosphonates are particularly advantageous for incorporation into biomaterials. Each molecule of a pentaphosphonate, for example, will have 2.5 times more phosphonate, on a molar basis, than EHDP. Thus, a greater amount of anticalcification agent can be irreversibly bound to the substrate material.

The calcification-resistant synthetic biomaterials of the present invention can be cast into molds; dissolved in solvents, such as DMA and THF, and cast into thin films or flexing leaflet membranes; combined with other compatible polymers; dip-coated on surfaces of other materials, including tissue-derived biomaterials to improve their biophysical stability.

EXPERIMENTAL SECTION

Synthetic Biomaterial in Rat Subdermal Model

The calcium content of calcification-resistant polyurethane specimens fabricated in accordance with the present invention was determined by atomic absorption spectroscopy following 60 days subdermal implantation in weanling male rats (3 weeks). The results are depicted on FIG. 4 which is a graphical illustration of the calcium content of several synthetic biomaterial specimens, in μg/mg, following subdermal implantation in a rat for 60 days.

Figure 4:
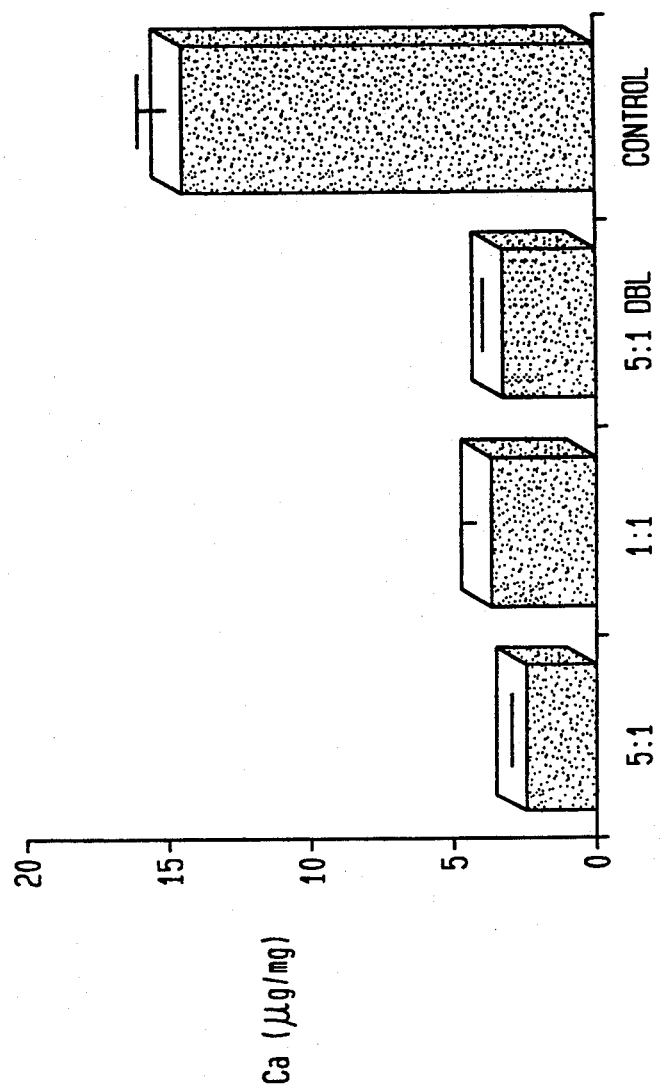
FIG. 4 is a graphical illustration of the calcium content ($\mu$g/mg) of several synthetic biomaterial specimens in accordance with the invention following subdermal implantation in rats for 60 days.

Synthetic biomaterial specimens were prepared in accordance with the method described above in Sec. B for the study shown in FIG. 3. The components of the synthetic biomaterial specimens were polyurethane (Mitrathane, MPU-5), ethanehydroxydiphosphonic acid (EHDP), and Denacol 521. Referring to FIG. 4, the legend "5:1" refers to a polyurethane-based polymer wherein the concentrations of the reactive binding components are 0.1M Denacol 521 to 0.02M EHDP; "1:1" refers to equimolar concentrations of EHDP and Denacol 521 (0.02M); and "5:1 dbl" refers to 0.2M Denacol 521 to 0.04M EHDP. The "control" was Mitrathane.

A calcification-resistant synthetic biomaterial specimen and a control specimen were implanted in two subcutaneous pouches dissected in the ventral abdominal wall of weanling rats (male, CD, Sprague-Dawley, weighing 50–60 gm). After a period of 60 days, the specimens were removed and examined for calcification by measuring the level of $Ca^{+2}$ ions.

Referring to FIG. 4, diphosphonate-derivatized Mitrathane polyurethane did not calcify following subdermal implantation in a rat for 60 days, whereas the control Mitrathane polyurethane implants did. Clearly, FIG. 4 demonstrates a statistically significant reduction in calcium content for the novel synthetic biomaterial specimens of the present invention as compared to the control.

In an alternative embodiment, derivitization of polytetramethyleneglycol prior to polymerization led to the synthesis of another EHDP derivatized polyurethane with a hydroxy-terminated polytetramethyleneglycol soft segment (2000 molecular weight). The resulting polymer was used as a surface coating on various substrates, specifically Mitrathane and glutaraldehyde cross-linked pericardium. Inhibition of calcification was studied in a 60 day rat subdermal model as reported above. The results are reported in Table III which gives the calcium content of the specimen, in μg/ng, following 60 days of implantation.

TABLE III

| Sample | N | $Ca^{++}$ (μg/mg) |
|---|---|---|
| Mitrathane (control) | 10 | 12.57 ± 0.86 |
| EHDP-Polyurethane (coated) | 10 | 0.25 ± 0.04 |
| GLT-crosslinked Pericardium | 10 | 226.9 ± 23.5 |
| Mitrathane (unimplanted) | 10 | 0.14 ± 0.004 |
| Pericardium (unimplanted) | 10 | 0.28 ± 0.004 |

As can be seen in Table III, the "epoxy-bridge incorporation" technique is suitable for the synthesis of calcification-resistant materials which may be used as coatings. The EHDP-epoxy-polyurethane coated Mitrathane did not calcify as compared to controls. Thus, epoxy-bridge formation with polyphosphonate effectively inhibits calcification irrespective of whether the calcification-resistant material is incorporated throughout the polymer matrix, or via a surface coating as demonstrated by the data in Table III.

The calcification-resistant materials of the present invention are ideally suited for any body-invasive uses in which pathologic calcification is a possibility. Such uses include, vascular grafts, pacemakers, numerous other prosthetic or implanted devices, such as artificial bone and hip joints, cosmetic implants of silicone, tendon prostheses, etc.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A method of making a calcification-resistant bicompatible polymeric material comprising the steps of:

forming a monoadduct of a polyphosphonate anticalcification agent and a reactive polyfunctional epoxide;

adding the monoadduct to a prepolymer base of a biocompatible copolymer;

adding the second component of the biocompatible copolymer; and polymerizing.

2. The method of claim 1 wherein the biocompatible copolymer is polyurethane.

3. The method of claim 2 wherein the prepolymer base is tetramethylene glycol and the second component is diisocyanate.

4. The method of claim 1 wherein the polyphosphonate is selected from the group consisting of aminopropanehydroxydiphosphonate, ethanehydroxydiphosphonate, aminomethyltriphosphonic acid, and butylpentaphosphonic acid.

5. The method of claim 1 wherein the polyfunctional epoxide is selected from the group consisting of diglycidyl butanediol ether, ethanediol diglycidyl ether, butanediol diglycidyl ether, and polyglycerol polyglycidyl ethers.

6. A method of making a calcification-resistant polymeric material comprising the steps of:

forming a solution of a polyphosphonate anticalcification agent and a reactive polyfunctional epoxide in a solvent;

adding to the solution a prepolymerized biocompatible polymer which is soluble in the solvent to form a mixture; and polymerizing the mixture.

7. The method of claim 6 wherein the polyphosphonate is selected from the group consisting of aminopropanehydroxydiphosphonate, ethanehydroxydiphosphonate, aminomethyltriphosphonic acid, and butylpentaphosphonic acid.

8. The method of claim 6 wherein the polyfunctional epoxide is selected from the group consisting of diglycidyl butanediol ether, ethanediol diglycidyl ether, butanediol diglycidyl ether, and polyglycerol polyglycidyl ethers.

* * * * *